United States Patent [19]

Magatti

[11] Patent Number: 4,468,396
[45] Date of Patent: Aug. 28, 1984

[54] ANTIHYPERTENSIVE BENZOTHIADIAZINES

[75] Inventor: Charles V. Magatti, Verona, N.J.

[73] Assignee: Schering Corporation, Kenilworth, N.J.

[21] Appl. No.: 450,865

[22] Filed: Dec. 20, 1982

[51] Int. Cl.³ .................... C07D 417/12; A61K 31/54
[52] U.S. Cl. ...................................... 424/246; 544/13
[58] Field of Search ..................... 260/243.3, 112.5 R; 544/13; 424/246

[56] References Cited

U.S. PATENT DOCUMENTS 4,338,435  7/1982  Haugwitz .............................. 544/13

FOREIGN PATENT DOCUMENTS 57-134469  8/1982  Japan .
2073187  10/1981  United Kingdom .

Primary Examiner—John M. Ford
Attorney, Agent, or Firm—Anita W. Magatti; Gerald S. Rosen

[57] ABSTRACT

This invention relates to benzothiadiazinyl-substituted carboxyalkyl dipeptides useful as combined antihypertensive and diuretic agents.

22 Claims, No Drawings

ANTIHYPERTENSIVE BENZOTHIADIAZINES

The present invention relates to benzothiadiazine-substituted carboxyalkyl dipeptide compounds which have combined antihypertensive and diuretic activity.

More particularly, this invention relates to compounds represented by the following formula:

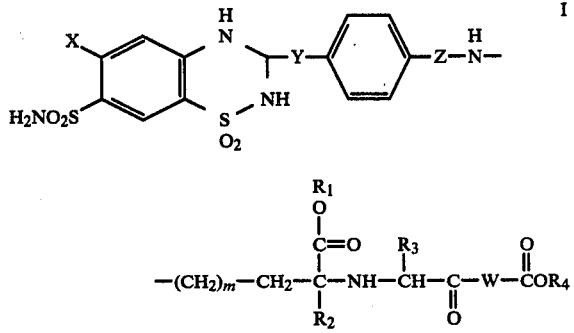

and the salts thereof, wherein W is

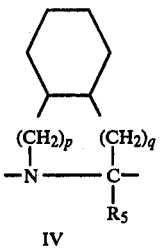 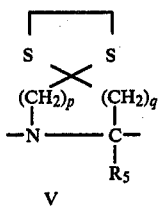

X is halogen or CF$_3$;
Y is —CH$_2$—, —CH$_2$O—, —CH$_2$S—, —CH$_2$OCH$_2$—, or —CH$_2$SCH$_2$—;
Z is sulfonyl or carbonyl;
R$_1$, R$_2$, R$_4$ and R$_5$ are hydrogen or lower alkyl;
R$_3$ is hydrogen, lower alkyl, or amino lower alkyl;
m is 0 to 5; and
p is 0, 1, or 2 and q is 0, 1, 2, provided that the sum of p and q is 1 or 2, and that in formula V p is not 0.

In a preferred embodiment, the present invention relates to compounds of formula I wherein W is represented by formula IV, p is 0 and q is 1, i.e. compounds of the formula VI

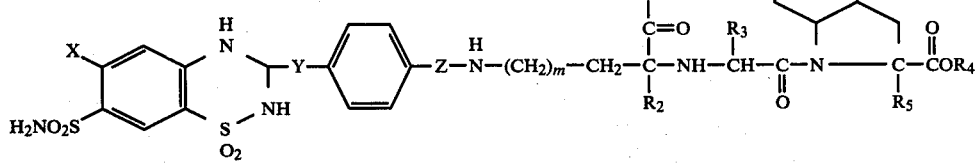

and the pharmaceutically acceptable salts thereof, wherein R$_1$, R$_2$, R$_3$, R$_4$, R$_5$, X, Y, Z and m are as defined above.

A second preferred embodiment relates to compounds of formula I wherein W is of formula V and p and q are each 1, i.e. compounds of formula VII

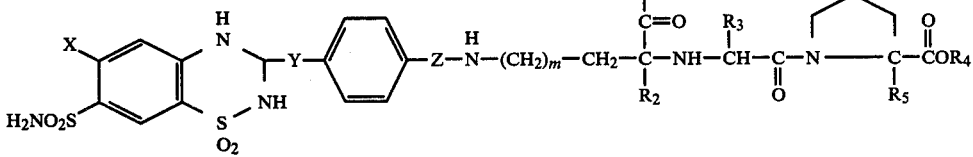

and the pharmaceutically acceptable salts thereof, wherein R$_1$, R$_2$, R$_3$, R$_4$, R$_5$, X, Y, Z and m are as defined above.

Preferred compounds of formula VI and VII are those in which R$_2$, R$_4$ and R$_5$ are hydrogen. Also preferred are those compounds wherein R$_1$ is hydrogen or lower alkyl and R$_3$ is lower alkyl. Another group of preferred compounds of formula VI and VII are those wherein m is 3. A fourth preferred group includes compounds wherein Y is —CH$_2$O—, and a fifth group includes compounds wherein Z is carbonyl. Most preferred are compounds of formula VI and VII wherein R$_2$, R$_4$ and R$_5$ and hydrogen, R$_1$ is hydrogen or lower

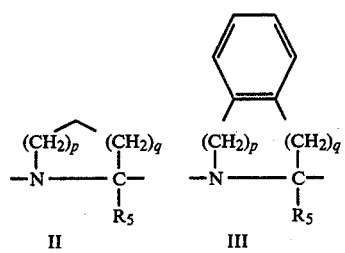

alkyl, $R_3$ is lower alkyl, m is 3, Y is —$CH_2O$—, and Z is carbonyl.

Preferred X-substituents on the benzothiadiazinyl group are halogen atoms, with chlorine being most preferred.

As used herein, "lower alkyl" means straight and branched chain hydrocarbon radicals of from 1 to 6 carbons, e.g. methyl, ethyl, propyl, isopropyl, butyl, iso-butyl, t-butyl, pentyl and hexyl and 'halogen' means fluorine, chlorine and bromine.

The aforementioned compounds of the instant invention include various stereoisomers. Preferred stereoisomers are those in which the configuration adjacent to the nitrogen atoms correspond most closely to natural L-aminoacids.

The compounds of this invention form salts with various inorganic and organic acids and bases which are also within the scope of the invention. Such salts include ammonium salts, alkali metal salts, e.g. sodium and potassium salts, and alkaline earth metal salts, e.g. calcium and magnesium salts. Salts with organic and inorganic acids may be prepared, e.g., HC, HBr, $H_2SO_4$, $H_3PO_4$, methanesulfonic acid, toluenesulfonic acid, maleic acid, fumaric acid and camphorsulfonic acid. The non-toxic pharmaceutically acceptable salts are preferred, although other salts are also useful, e.g., in isolating or purifying the product. The acid salts (e.g. HC and maleate) are preferred, especially the hydrochloride.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Compounds of the this invention are prepared by using known coupling methods as indicated in the following reaction schemes:

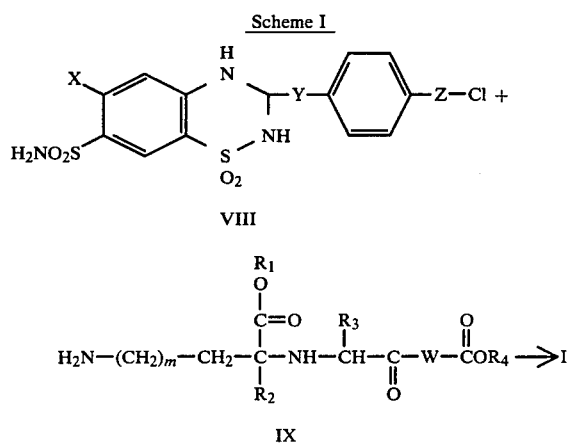

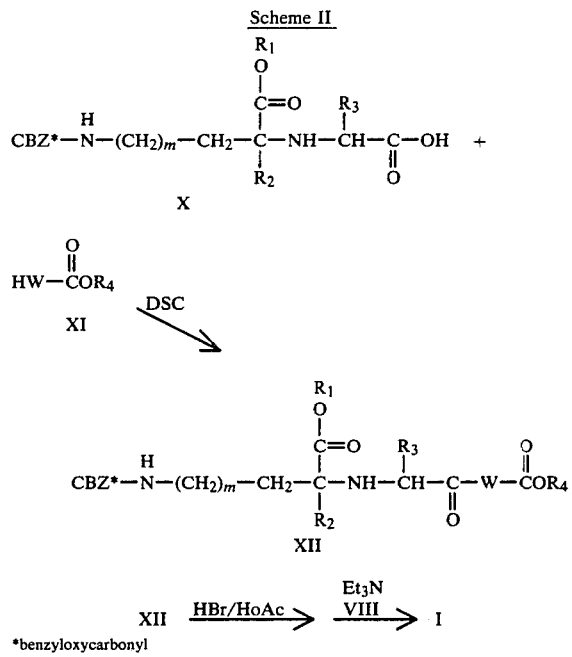

*benzyloxycarbonyl

In this procedure, an acid chloride of formula VIII is reacted with an aminoacid compound of formula IX to obtain a compound of formula I. The reaction is carried out in a solvent such as tetrahydrofuran or methylene chloride in the presence of a base such as triethylamine at room temperature.

In this procedure, the N-protected alkylamino acid is converted to an activated ester and reacted with a cyclic or aromatic amino acid of formula XI in a solvent such as acetonitrile to give the protected dipeptide of formula XII. This compound is deprotected and converted to the hydrobromide salt, then reacted with an acid chloride of formula VIII in the same manner as in Reaction Scheme I to give the product of formula I.

This second method is preferred for preparing compounds wherein W is of formula V.

The known coupling methods above include amino group protection during the coupling reaction, for example by N-formyl, N-t-butoxycarbonyl, and N-carbobenzyloxy groups followed by their removal to yield I. Furthermore, the carboxylic acid function at the 2-position of the ring in formulae IX and XI may be protected by removable ester groups such as benzyl, ethyl, t-butyl and the like.

Condensing agents in this synthetic route are typically those useful in peptide chemistry such as dicyclohexylcarbodiimide (DCC) or diphenylphosphoryl azide (DPPA) or compounds of formula X may be activated via the intermediacy of activated esters such as that derived from N-hydroxysuccinimide, disuccinimidyl carbonate (DSC), and the like.

The starting materials of formula VIII may be prepared using techniques known in the art and described in Preparation 1.

The starting materials of formulae IX, X and XI are similarly prepared by known techniques, and are described in Preparations 2, 4 and 3, respectively.

PREPARATION 1

6-CHLORO-7-SULFAMYL-3-(4-CHLOROCARBONYLPHENOXYMETHYL)-3,4-DIHYDRO-2-H-1,2,4-BENZOTHIADIAZINE-1,1-DIOXIDE (A) Methyl-4-[2',2'-diethoxy]-ethoxy benzoate Combine methyl-4-hydroxybenzoate (7.6 g, 0.06 moles), and potassium t-butoxide (5.6 g, 0.057 moles) in dry dimethylformamide (100 ml) and heat to 120° C.

while stirring under nitrogen. Add bromoacetaldehyde diethylacetal (10.0 g, 0.05 mole) dropwise and heat at 120° C. for 20 hours. Cool the reaction mixture, filter off the solid material and evaporate in vacuo. Suspend the resultant residue in water and extract with diethyl ether. Wash the organic layer with 10% sodium hydroxide and again with water. Dry the organic layer over anhydrous sodium sulfate and evaporate in vacuo to yield the title compound as a yellow oil. Mass Spectrum M+ =268, NMR: 1.20 (6H, t, —CH$_3$), 3.70 (4H, M, —OCH$_2$—), 3.80 (3H, , CH$_3$), 4.05 (2H, , CH$_2$), 4.80 (1H, t, CH—), 7.45 (4H, AA', BB', Ar).

(B) 4-[2',2'-Diethoxy]-ethoxy benzoic acid

Dissolve sodium hydroxide pellets (1.0 g) in ethanol (10 ml) and water (2 ml). Add the product of Step A (1.0 g, 0.0037 mole) and stir at room temperature for 4 hours. Evaporate the resultant mixture in vacuo to obtain a white gum. Dissolve the resultant gum in water, adjust to pH5 with tartaric acid, and extract the solution with diethyl ether. Wash the organic layer with water, then dry the organic layer with anhydrous sodium sulfate. Evaporate the solvent in vacuo, then recrystallize the resultant residue from ethyl acetate/hexane to obtain the title compound, m.p. 114°–115° C.

(C) 6-Chloro-7-sulfamyl-3-(4-carboxyphenoxymethyl)-3,4-dihydro-2H-1,2,4-benzothiadiazine-1,1-dioxide Stir 5-chloroaniline-2,4-disulfonamide (0.74 g, 0.0026 moles) and the product of Step B (0.74 g, 0.0029 moles) in dimethoxyethane (10 ml) and add concentrated hydrochloric acid (2 drops). Reflux the resultant mixture for four hours, then evaporate the solvent in vacuo. Triturate the resultant slurry with hexane, then wash the resultant white crystalline product in ethanol and filter to obtain the title compound, m.p. 276°–277° C. (dec.).

(D) 6-Chloro-7-sulfamyl-3-(4-chlorocarbonylphenoxymethyl)-3,4-dihydro-2-H-1,2,4-benzothiadiazine-1,1-dioxide Dissolve the product of Step C (0.5 g, 1.1 moles) in dimethylformamide (1 ml) and add chloroform (10 ml) to obtain a slurry. Cool the resultant mixture to 5° C. and add thionyl chloride (15 ml) dropwise over a 30 minute period. Stir an additional hour at 5° C., then concentrate in vacuo at room temperature to obtain the title compound as a light yellow oil which may be used without further purification.

PREPARATION 2

1-{N-[1(S)-ETHOXYCARBONYL-5-AMINOPENTYL]-(S)-ALANYL}-OCTAHYDRO-1H-INDOLE-2(S)-CARBOXYLIC ACID (A) N-Pyruvoyl-octahydro-1H-indole-2-(S)-carboxylic acid benzyl ester Cool a solution of octahydro-1H-indole-2-(S)-carboxylic acid benzyl ester d-10-camphorsulfonic acid salt (27 g) in dichloromethane (300 ml) and pyridine (26.1 g) to 5° C. under nitrogen. Add, dropwise and with stirring, a solution of pyruvoyl chloride (11.8 g) in dichloromethane (200 ml). Allow the solution to warm to 25° C. and stir for 24 hours. Wash the resultant solution with 1N hydrochloric acid (1 liter), then with saturated aqueous sodium carbonate (1 liter). Dry the organic layer over anhydrous magnesium sulfate and evaporate in vacuo. Distill the resulting residue (bulb to bulb, air bath 200° C., 0.02 mm/Hg) to obtain the title compound.

The product may be further purified by triturating with pentane to give a tan solid, m.p. 50°–55° C.

(B) 1-{N-[1-(S)-Ethoxycarbonyl-5-(N-benzyloxycarbonylamino)-pentyl]-(S)-alanyl}-octahydro-1H-indole-2-(S)-carboxylic acid benzyl ester Cool a solution of N-ε-benzyloxycarbonyl-L-lysine ethyl ester (25 g) and the product of Step A (8.8 g) in dry ethyl ether (800 ml) to 5° C. under nitrogen. Add, dropwise and with stirring over a period of two hours, a solution of titaniun tetrachloride (2.56 g) in hexane (400 ml). Stir the resultant mixture an additional 18 hours at 25° C., then evaporate the solvent in vacuo at 25° C. Slurry the residue in ethanol (1 liter), add sodium cyanoborohydride (5.1 g); and stir under nitrogen for 18 hours. Evaporate the solvent at 25° C. in vacuo, slurry the resultant residue in ethyl acetate (1 liter), adjust to pH 8 with 1N sodium hydroxide and filter. Extract the aqueous layer with ethyl acetate (600 ml), combine the organic layers and dry the combined layers over anhydrous magnesium sulfate. Evaporate the solvent in vacuo at 25° C. Separate the isomer by chromatographing the resulting oil on silica gel (1.7 kg.), eluting with ethyl acetate:ether (1:1). Thin layer chromatography (ethyl acetate as eluent) shows the S-isomer at Rf=0.5 and the R isomer at Rf=0.4.

(C) 1-{N-[1(S)-Ethoxycarbonyl-5-aminopentyl]-(S)-alanyl}-octahydro-1H-indole-2-(S)-carboxylic acid Dissolve the product of Step B (S-alanyl isomer) (2 g) in ethanol (25 ml), add 20% Pd(OH)$_2$/C (0.3 g) and hydrogenate at 60 psi on a Parr shaker for 2 days. Filter the mixture and concentrate the filtrate at 25° C. in vacuo. Triturate the resulting oil with ether to obtain the title compound as a white solid, m.p. 160° C. (dec).

The (R)-alanyl isomer may be similarly prepared, m.p. 105° C. (dec).

PREPARATION 3

1,4-DITHIA-7-AZASPIRO[4.4]NONANE-8(S)-CARBOXYLIC ACID

A. Dissolve 1-benzyloxycarbonyl-4-keto-(S)-proline ethyl ester in glacial acetic acid. Add p-toluenesulfonic acid and 1,2-ethanedithiol and heat under reflux with stirring for eighteen hours. Add the reaction mixture to saturated sodium bicarbonate solution and extract with ethyl acetate. Dry the organic layer over magnesium sulfate and concentrate it. Place the residue on a column of silica gel (300 g, 60–200 mesh) and elute with hexane:ethyl acetate (1:1) to give 7-benzyloxycarbonyl-1,4-dithia-7-azaspiro[4.4]nonane-8(S)-carboxylic acid ethyl ester, a yellow oil having $[\alpha]_D^{26} = -21.0°$ (ethanol).

B. Dissolve the product of Step A in 20 ml of 20% hydrobromic acid in glacial acetic acid and stir the mixture at room temperature for two hours. Add the mixture dropwise to diethyl ether at 0°–5° C. to give 1,4-dithia-7-azaspiro[4.4]nonane-8(S)-carboxylic acid ethyl ester hydrobromide.

C. Dissolve the product of Step B in 0.1N NaOH and extract with ethyl acetate. Dry the organic layer over magnesium sulfate and concentrate in vacuo to give 1,4-dithia-7-azaspiro[4.4]nonane-8(S)-carboxylic acid ethyl ester.

PREPARATION 4

1-{N-[1(S)-ETHOXYCARBONYL-5-(N-BENZYLOXYCARBONYLAMINO)PENTYL]-(S)-ALANINE}

A. N-E-Benzyloxycarbonyl-L-lysine ethyl ester

Dissolve N-E-N-benzyloxycarbonyl-L-lysine (100 g, 0.347 moles) in ethanol (1600 ml), add boron trifluoride etherate (220 ml, 1.76 moles) (freshly distilled from calcium hydride at 10 mm/Hg) and reflux 60 hours. Evaporate the solvent in vacuo, dissolve the resultant residue in water (900 ml) and extract with ether ($3 \times 300$ ml). Cool the aqueous layer to 10° C., adjust to pH 9 with 50% sodium hydroxide, add ethyl acetate (2 liters), and stir. Filter the resultant solid, then saturate the filtrate with sodium chloride. Wash the organic layer with brine, dry over anhydrous magnesium sulfate and evaporate the solvent at 30° C. to yield the title compound as a light yellow oil (88 g.)

B. 1-{N-[1(S)-Ethoxycarbonyl-5-(N-benzyloxycarbonylamino)pentyl]-(S)-alanine}tert-butyl ester Dissolve the product of Step A in dimethylformamide, add t-butyl-2-bromopropionate (90 g, 0.43 moles) and triethylamine (22 g, 0.22 moles), and stir at 70° C. (oil bath) overnight. Evaporate the solvent in vacuo. Add water (1 liter) to the resultant residue and extract with ether (1 liter). Dry the organic layer over anhydrous magnesium sulfate and evaporate the solvent to obtain the title compound as an orange oil (96 g). Thin layer chromatography indicates two isomers. Separate the isomers by chromatography, eluting with diethyl ether/hexane (1:1). The less mobile compound is the desired S,S isomer.

(C) 1-{N-[1(S)-Ethoxycarbonyl-5-(N-benzyloxycarbonylamino)pentyl}-(S)-alanine Cool dioxane (50 ml) in an ice bath, bubble in hydrochloride gas until saturated, and add the product of Step B. Stir under nitrogen overnight at room temperature. Evaporate the solvent to obtain a colorless oil. Triturate the oil with ether ($3 \times 20$ ml) and dry under vacuum to obtain the title compound as a white solid (240 mg).

EXAMPLE 1

1-{N-[1(S)-ETHOXYCARBONYL-5-[4-[(6-CHLORO-3,4-DIHYDRO-7-SULFAMYL-2H-1,2,4-BENZOTHIADIAZIN-3-YL-1,1-DIOXIDE)METHYIOXY)PHENYLCARBOXAMIDO]PENTYL]-(S)-ALANYL}-OCTAHYDRO-1H-INDOLE-2(S)-CARBOXYLIC ACID

Suspend the product of Preparation 2 (0.48 g, 0.7 mmole) in dry tetrahydrofuran (40 ml) containing triethylamine (0.55 ml, 4 eq.) and cool at 5° C. With stirring, over 30 minutes, add the product of Preparation 1 (0.32 g, 1 e.q.) in dry tetrahydrofuran (20 ml). Stir at room temperature for 1 hour, filter, and evaporate the solvent in vacuo. Dissolve the resultant residue in methylene chloride and acidify with HCl gas. Triturate the resultant gummy precipitate in methylene chloride to obtain the title compound as a white solid.

In a similar manner, using appropriate reactants, prepare the following compounds:

1-{N-[1(S)-ethoxycarbonyl-2-[4-[(6-chloro-3,4-dihydro-7-sulfamyl-2H-1,2,4-benzothiadiazin-3-yl-1,1-dioxide)methyloxy]phenylcarboxamido]ethyl]-(S)-alanyl}-octahydro-1H-indole-2(S)-carboxylic acid;

1-{N-[1(S)-carboxy-2-[4-[(6-chloro-3,4-dihydro-7-sulfamyl-2H-1,2,4-benzothiadiazin-3-yl-1,1-dioxide)methyl]phenylcarboxamido]ethyl]-(S)-alanyl}-octahydro-1H-indole-2(S)-carboxylic acid;

1-{N-[1(S)-ethoxycarbonyl-3-[4-[(6-chloro-3,4-dihydro-7-sulfamyl-2H-1,2,4-benzothiadiazin-3-yl-1,1-dioxide)methyloxy]phenylcarboxamido]propyl]-(S)-alanyl}-octahydro-1H-indole-2(S)-carboxylic acid;

1-{N-[1(S)-carboxy-5-[4-[6-chloro-3,4-dihydro-7-sulfamyl-2H-1,2,4-benzothiodiazin-3-yl-1,1-dioxide)methyloxy]phenylcarboxamido)pentyl]-(S)-alanyl}-octahydro-1H-indole-2(S)-carboxylic acid;

1-{N-[1(S)-carboxy-3-[4[(6-chloro-3,4-dihydro-7-sulfamyl-2H-1,2,4-benzothiadiazin-3-yl-1,1-dioxide)methyloxy]phenylcarboxamido]propyl]-(S)-alanyl}-octahydro-1H-indole-2(S)-carboxylic acid;

1-{N-[1(S)-ethoxycarbonyl-4-[4[(6-chloro-3,4-dihydro-7-sulfamyl-2H-1,2,4-benzothiadiazin-3-yl-1,1-dioxide)methyloxy]phenylcarboxamido]butyl]-(S)-alanyl}-octahydro-1H-indole-2(S)-carboxylic acid;

1-{N-[1(S)-carboxy-4-[4-[(6-chloro-3,4-dihydro-7-sulfamyl-2H-1,2,4-benzothiadiazin-3-yl-1,1-dioxide)methyloxy]phenylcarboxamido]butyl]-(S)-alanyl}-octahydro-1H-indole-2(S)carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyl]phenylcarboxamido]pentyl]-(S)-alanyl}-octahydro-1H-indole-2(S)carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methylthio]phenylcarboxamido]pentyl]-(S)-alanyl}-octahydro-1H-indole2(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]benzylcarboxamido]pentyl]-(S)-alanyl}-octahydro-1H-indole-2(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methylthio]benzylcarboxamido]pentyl]-(S)-alanyl}-octahydro-1H-indole-2(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]phenylsulfonamido]pentyl]-(S)-alanyl}-octahydro-1H-indole-2(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyl]phenylsulfonamido]pentyl]-(S)-alanyl}-octahydro-1H-indole-2(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methylthio]phenylsulfonamido]pentyl]-(S)-alanyl}-octahydro-1H-indole-2(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]benzylsulfonamido]pentyl]-(S)-alanyl}-octahydro-1H-indole-2(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methylthio]benzylsulfonamido]pentyl]-(S)-alanyl}-octahydro-1H-indole-2(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]phenylcarboxamido]pentyl]-(S)-alanyl}-(S)-proline;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]phenylcarboxamido]pentyl]-(S)-alanyl}-1,2,3,4-tetrahydroisoquinoline-3(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]phenylcarboxamido]pentyl]-(S)-alanyl}-decahydroquinoline-3(S)-carboxylic acid;

1-{N-[1(S)-ethoxycarbonyl-5-[4-[(6-trifluoromethyl-3,4-dihydro-7-sulfamyl-2H-1,2,4-benzothiadiazin-3-yl-1,1-dioxide)methyloxy]phenylcarboxamido]pentyl](S)-alanyl}-octahydro-1H-indole-2(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]phenylcarboxamido]pentyl]-(S)-lysyl}-octahydro-1H-indole2(S)-carboxylic acid.

EXAMPLE 2

1-{N-[1(S)-ETHOXYCARBONYL-5-[4-[(6-CHLORO-3,4-DIHYDRO-7-SULFAMYL-2H-1,2,4-BENZOTHIADIAZIN-3-YL-1,1-DIOXIDE)METHYLOXY]PHENYLCARBOXAMIDO]PENTYL]-(S)-ALANYL}-1,4-DITHIA-7-AZASPIRO[4.4]NONANE-8(S)-CARBOXYLIC ACID (A)

1-{N-[1(S)-Ethoxycarbonyl-5-(N-benzyloxycarbonylamino)pentyl]-(S)-alanyl}-1,4-dithia-7-azaspiro[4.4]nonane-8(S)-carboxylic acid Dissolve the product of Preparation 4 (0.818 g, 0.0022 moles) in acetonitrile (30 ml), add disuccinimidylcarbonate (0.66 g, 1 eq.) dry pyridine (0.18 ml, 1 eq.), and stir for 48 hours. Dissolve the product of Preparation 3 (0.46 g, 1 eq.) in acetonitrile, add dropwise to the above reaction mixture, and stir an additional 24 hours. Evaporate the solvent in vacuo, dissolve the resultant residue in ethyl acetate, wash with water and then brine. Dry the organic layer over anhydrous sodium sulfate, filter and evaporate the solvent in vacuo to obtain the title compound as an oil.

(B)

1-{N-[1(S)-Ethoxycarbonyl-5-aminopentyl]-(S)-alanyl}-1,4-dithia-7-azaspiro[4.4]nonane-8(S)-carboxylic acid hydrobromide Combine the product of Step A with 20% hydrobromic acid in glacial acetic acid (10 ml) and stir for 3 hours. Evaporate the solvent in vacuo and triturate the resultant residue with ether to obtain the title compound.

(C) In a manner similar to that described in Example 1, treat the product of Step B with 3 equivalents of triethylamine and add the product of Preparation 4 to obtain the title compound.

In a similar manner, using appropriate reactants, prepare the following compounds:

1-{N-[1(S)-carboxy-5-[4-[(6-chloro-3,4-dihydro-7-sulfamyl-2H-1,2,4-benzothiadiazin-3-yl-1,1-dioxide)methyloxy]phenylcarboxamido]pentyl]-(S)-alanyl}-1,4-dithia-7-azaspiro[4.4]nonane-8(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyl]phenylcarboxamido]pentyl]-(S)-alanyl}-1,4-dithia-7-azaspiro[4.4]nonane-8(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methylthio]phenylcarboxyamido]pentyl]-(S)-alanyl}-1,4-dithia-7-azaspiro[4.4]nonane-8(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]benzylcarboxamido]pentyl]-(S)-alanyl}-1,4-dithia-7-azaspiro[4.4]nonane-8(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methylthio]benzylcarboxyamido]pentyl]-(S)-alanyl}-1,4-dithia-7-azaspiro[4.4]nonane-8(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]phenylsulfonamido]pentyl]-(S)-alanyl}-1,4-dithia-7-azaspiro[4.4]nonane-8(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyl]phenylsulfonamido]pentyl]-(S)-alanyl}-1,4-dithia-7-azaspiro[4.4]nonane-8(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methylthio]phenylsulfonamido]pentyl]-(S)-alanyl}-1,4-dithia-7-azaspiro[4.4]nonane-8(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methyloxy]benzylsulfonamido]pentyl]-(S)-alanyl}-1,4-dithia-7-azaspiro[4.4]nonane-8(S)-carboxylic acid;

1-{N-[1(S)-ethoxycarbonyl-5-[4-[(6-chloro-3,4-dihydro-7-sulfamyl-2H-1,2,4-benzothiadiazin-3-yl-1,1-dioxide)methylthio]benzylsulfonamido]pentyl]-(S)-alanyl}-1,4-dithia-7-azaspiro[4.4]nonane-8(S)-carboxylic acid;

The compounds of this invention are useful in view of their pharmacological properties. In particular, they possess activity both as antihypertensive agents, as evidenced by their ability to reduce blood pressure in mammals in which the blood pressure has become abnormally elevated and as diuretic agents.

Since these compounds are believed to act as angiotensin converting enzyme inhibitors, it is also contemplated that they may be used in treating other cardiovascular disorders, for example congestive heart failure, in the same manner as other ACE inhibitors such as captopril and MK-421 may be used.

The compounds of this invention can be combined with pharmaceutical carriers and administered in a variety of well-known pharmaceutical forms suitable for oral or parenteral administration to provide compositions useful in the treatment of cardiovascular disorders and particularly mammalian hypertension.

The effective daily antihypertensive dose (ED$_{50}$) of the compounds of this invention will typically be in the range of about 0.1 to about 25 mg/kg, of mammalian weight, administered in single or divided doses. The exact dose to be administered is determined by the attending clinician and is dependent upon where the particular compound lies within the above quoted range, as well as upon the age, weight and condition of the individual.

Generally, in treating humans having hypertension, the compounds of this invention may be administered to patients in need of such treatment in a dosage range of about 5 to about 500 mg per patient generally given several times a day, thus giving a total daily dose of from about 5 to about 2000 mg per day.

The antihypertensive compositions containing the compounds of this invention will preferably contain from about 5 to about 250 mg of the active compound per dosage unit.

The compositions of the present invention are most preferably administered orally. Typical formulations for oral administration are those such as tablets, capsules, syrups, elixirs or suspensions. Typical injectable formulations include solutions and suspensions. Also contemplated are mechanical delivery systems, e.g. transdermal dosage forms.

In the following examples, the "active ingredient" is 1-N-{[1(S)-ethoxycarbonyl-5-[4-[(6-chloro-3,4-dihydro-7-sulfamyl-2H-1,2,4-benzothiodiazin-3-yl-1,1-dioxide)-methyl]phenylcarboxamido]pentyl]-(S)-alanyl}-octahydro-1H-indole-2(S)-carboxylic acid. It is contemplated, however, that this compound may be replaced by equally effective quantities of other compounds within the scope of formula I.

EXAMPLE 3

| Capsule | Amount (mg) | |
|---|---|---|
| Active ingredient | 250.0 | 125.0 |
| Lactose | 173.0 | 86.5 |
| Corn Starch | 75.0 | 37.5 |
| Magnesium stearate | 2.0 | 1.0 |
| | 500.0 | 250.0 |

Blend the active ingredient, lactose, and corn starch until uniform; then blend the magnesium stearate into the resulting powder. Encapsulate the mixture into suitably sized two-piece hard gelatin capsules.

EXAMPLE 4

| Tablet | Amount (mg) | |
|---|---|---|
| Active Ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 5

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°–70° C. and cool the solution to 25°–35° C. Charge and dissolve all other excipients and the active ingredient. Bring the solution to final volume, filter it through a sterilizing membrane and fill into sterile containers.

Similarly, substitute other compounds of the present invention (for example, the title compound of Example 6 or the title compound of Example 7) to prepare other compositions of the present invention.

I claim:

1. A compound represented by the formula

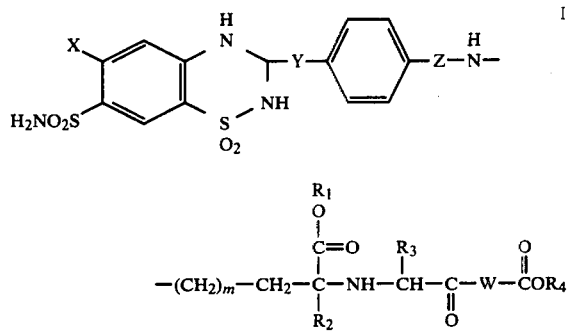

and the salts thereof, wherein
W is

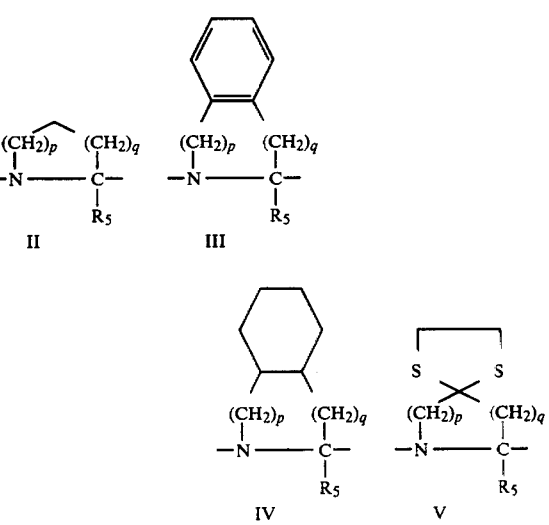

X is halogen or CF$_3$;
Y is —CH$_2$—, —CH$_2$O—, —CH$_2$S—, —CH$_2$OCH$_2$—, or —CH$_2$SCH$_2$—;
Z is sulfonyl or carbonyl;

$R_1$, $R_2$, $R_4$ and $R_5$ are hydrogen or lower alkyl;
$R_3$ is hydrogen, lower alkyl, or amino lower alkyl;
m is 0 to 5; and
p is 0, 1 or 2 and q is 0, 1 or 2, provided that the sum of p and q is 1 or 2, and that in formula V p is not 0.

2. A compound of claim 1 wherein said salts are non-toxic, pharmaceutically acceptable salts.

3. A compound of claim 2 wherein Z is carbonyl.

4. A compound of claim 2 wherein Y is —$CH_2O$—.

5. A compound of claim 2 wherein X is halogen.

6. A compound of claim 5 wherein X is chlorine.

7. A compound of claim 2 wherein $R_2$, $R_4$ and $R_5$ are hydrogen.

8. A compound of claim 2 wherein $R_1$ is hydrogen or lower alkyl and $R_3$ is lower alkyl.

9. A compound of claim 2 wherein W is

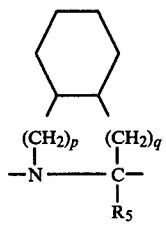

10. A compound of claim 9 wherein p is 0 and q is 1.

11. A compound of claim 10 wherein Z is carbonyl and X is chloro.

12. A compound of claim 11 wherein $R_2$, $R_4$ and $R_5$ are hydrogen and $R_1$ and $R_3$ are lower alkyl.

13. A compound of claim 12 wherein Y is —$CH_2O$—.

14. A compound of claim 13 wherein m is 3, R is ethyl, and $R_3$ is methyl, said compound being 1-N-[1(S)-ethoxycarbonyl-5-[4-[(6-chloro-3,4-dihydro-7-sulfamyl-2$\underline{H}$-1,2,4-benzothiadiazin-3-yl-1,1-dioxide)methoxy]phenylcarboxamido]pentyl]-(S)alanyl-octahydro-1H-indole-2(S)-carboxylic acid.

15. A compound of claim 2 wherein W is

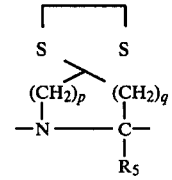

16. A compound of claim 15 wherein p and q are each 1.

17. A compound of claim 15 wherein z is carbonyl and X is chloro.

18. A compound of claim 17 wherein $R_2$, $R_4$ and $R_5$ are hydrogen, $R_1$ is hydrogen or lower alkyl and $R_3$ is lower alkyl.

19. A compound of claim 18 wherein Y is —$CH_2O$—.

20. A compound of claim 16 wherein m is 3, R is ethyl and $R_3$ is methyl, said compound being 1N-[1(S)-ethoxycarbonyl-5-[4-[(6-chloro-3,4-dihydro-7-sulfamyl-2$\underline{H}$-1,2,4-benzothiadiazin-3-yl-1,1-dioxide)methyloxy]phenylcarboxamido]pentyl]-(S)-alanyl-1,4-dithia-7-azaspiro[4.4]nonane-8(S)-carboxylic acid.

21. A composition comprising an antihypertensive and diuretic effective amount of a compound of claim 2 in a pharmaceutically acceptable carrier.

22. A method of treating hypertension in mammals comprising administering to a mammal in need of such treatment an antihypertensive and diuretic effective amount of a composition of claim 2.

* * * * *